United States Patent [19]

Powers

[11] Patent Number: 4,847,202
[45] Date of Patent: Jul. 11, 1989

[54] HETEROCYCLIC INHIBITORS OF SERINE PROTEASES

[75] Inventor: James C. Powers, Atlanta, Ga.

[73] Assignee: Georgia Tech Research Institute, Atlanta, Ga.

[21] Appl. No.: 844,344

[22] Filed: Mar. 26, 1986

Related U.S. Application Data

[62] Division of Ser. No. 492,825, May 9, 1983, Pat. No. 4,585,793.

[51] Int. Cl.[4] .................. C07D 265/12; C07D 239/72; C07D 217/22; C12N 9/99
[52] U.S. Cl. ................................. 435/184; 514/230.5; 514/259; 514/309; 514/307; 514/432; 514/460; 514/456; 435/213; 435/218; 435/219; 544/286; 544/283; 544/92; 544/93; 546/141; 546/142
[58] Field of Search ................... 544/286, 283, 92, 93; 546/141, 142; 514/236, 259, 226, 227, 222, 309, 307, 432, 460, 456

[56] References Cited

U.S. PATENT DOCUMENTS

| | | | |
|---|---|---|---|
| 3,772,304 | 11/1973 | Grethe et al. | 546/141 |
| 4,465,687 | 8/1984 | Doherty et al. | 514/210 |
| 4,469,885 | 9/1984 | Mueller et al. | 562/459 |
| 4,493,839 | 1/1985 | Doherty et al. | 514/210 |

OTHER PUBLICATIONS

Kleinerman et al., Am. Rev. Respir. Dis., 1981, pp. 714-717.

Primary Examiner—Richard A. Schwartz
Assistant Examiner—Robert C. Whittenbaugh
Attorney, Agent, or Firm—Hurt, Richardson, Garner, Todd & Cadenhead

[57] ABSTRACT

Certain novel heterocyclic compounds, aromatic thioesters, their preparation, and their use in inhibiting serine proteases with chymotrypsin-like and elastase-like specificity and in the treatment of diseases such as emphysema which involve tissue proteolysis.

3 Claims, No Drawings

HETEROCYCLIC INHIBITORS OF SERINE PROTEASES

This is a divisional of co-pending application Ser. No. 492,825 filed on May 9, 1983, now U.S. Pat. No. 4,585,793.

BACKGROUND OF THE INVENTION

This invention relates to a novel class of heterocyclic and aromatic compounds useful for selectively inhibiting elastase, selectively inhibiting chymotrypsin-like enzymes, or for generally inhibiting serine proteases of the elastase and chymotrypsin class. Certain clinical symptoms found in pancreatitis, emphysema, rheumatoid arthritis, inflammation, and adult respiratory distress syndrome are believe to be caused by uncontrolled elastase in the affected tissues. Likewise, similar clinical symptoms found in the same diseases are believed to be caused by uncontrolled cathepsin G, mast cell chymase, and other chymotrypsin-like enzymes. In vitro, proteolysis by serine proteases of the elastase and chymotrypsin families is often a severe problem in the production, isolation, purification, transport and storage of valuable peptides and proteins.

It is an object of this invention to find a novel group of specific inhibitors for elastase, chymotrypsin and other serine proteases of similar substrate specificity. Chymotrypsin and chymotrypsin-like enzymes normally cleave peptide bonds in proteins and peptides where the amino acid residue on the carbonyl side of the split bond ($P_1$ residue) is typically Trp, Tyr, Phe, Met, Leu or other amino acid residues which contain aromatic or large alkyl side chains. Elastase and elastase-like enzymes, on the other hand, cleave peptide bonds where the $P_1$ amino acid residue is much smaller, typically Ala, Val, Ser, Leu and other similar amino acids. All of the above enzymes have extensive secondary specificity and recognize amino acid residues removed from the $P_1$ residue. The inhibitors of this invention would be useful for treating diseases such as pancreatitis, emphysema, rheumatoid arthritis, adult respiratory distress syndrome, and inflammatory diseases which involve destruction of tissue by serine proteases. In some cases, it would be more useful to utilize a specific elastase or chymotrypsin-like enzyme inhibitor, while in other cases an inhibitor with broader specificity would be appropriate.

It is an object of this invention to find a novel group of specific inhibitors useful in vitro for inhibiting elastase, chymotrypsin and other serine proteases of similar specificity. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, or other proteins which are widely sold for use in clinical analysis, biomedical research, and for many other reasons. For some uses a specific inhibitor would be desirable, while in other cases, an inhibitor with general specificity would be preferred.

DETAILED DESCRIPTION OF THE INVENTION

Certain fluorinated acyl anthranilic acid thioesters have been found to be excellent inhibitors of human leukocyte elastase, porcine pancreatic elastase, bovine chymotrypsin and human cathepsin G. These compounds inhibit the serine proteases by reversibly blocking the enzyme and may be used in vivo to treat diseases resulting from tissue destruction due to elastase, chymotrypsin and related enzymes. They may be used in vitro to prevent proteolysis that occurs during the production, isolation, purification, storage, and transport of peptides and proteins. The novel fluorinated anthranilic acid thioesters have the following structural formula:

$$2-(R-Y-X)-C_6H_4-CO-S-R'$$

wherein

R' is selected from the group consisting of $C_{1-6}$ alkyl (such as ethyl, 2-methylpropyl, 2-methylbutyl, and 3-methylbutyl) and $C_{1-4}$ alkyl with an attached phenyl group (such as benzyl and 3-phenylpropyl), X is selected from the group consisting of NH, O, S, $CH_2$, and $CF_2$, Y is selected from the group consisting of CO, S, SO, O, $CF_2$, NH, and $CH_2$, R is selected from the group consisting of $C_{1-5}$ alkyl (such as ethyl), $C_{1-5}$ fluorinated alkyl (such as trifluoromethyl, pentafluoroethyl, and heptafluoropropyl), and $C_{1-5}$ alkoxy (such as t-butyloxy).

The subtituents on the aromatic ring of the above structure must be ortho to each other and not meta or para. The aromatic ring could be replaced by heterocyclic rings such as pyridine or a thiadiazole ring. The $C_6H_4$ could be replaced by a cis double bond or substituted double bond such as —CH=CH—, —CMe=CH—, —CMe=CMe—, (Me=methyl), or —CCF$_3$=CCF$_3$—.

Both R and R' could contain other groups or atoms such as O, or S in place of $CF_2$ or $CH_2$ groups as long as the substitution does not alter the uncharged hydrophobic character of R and R'.

The following novel compounds are representative of the invention:

N-trifluoroacetylanthranilic acid thioethyl ester,

N-trifluoroacetylanthranilic acid 2-methylpropyl thioester,

N-trifluoroacetylanthranilic acid 2-methylbutyl thioester,

N-trifluoroacetylanthranilic acid 3-methylbutyl thioester,

N-trifluoroacetylanthranilic acid thiobenzyl ester,

N-trifluoroacetylanthranilic acid 3-phenylpropyl thioester,

N-t-butyloxycarbonyl anthranilic acid thiobenzyl ester,

N-acetyl anthranilic acid thiobenzyl ester,

N-trifluoroacetyl anthranilic acid thiobenzyl ester,

N-pentafluoropropanoyl anthranilic acid thiobenzyl ester, and

N-heptafluorobutanoyl anthranilic acid thiobenzyl ester.

When R-X-Y is $CF_3CONH$ and R' is any of the noted groups, the thioester is a general inhibitor for both human leukocyte elastase (HL) and bovine chymotrypsin. Although these thioesters are slightly less effective toward porcine pancreatic (PP) elastase and cathepsin G, they are still capable of inhibiting these enzymes. The inhibition constants for the various inhibitors with chymotrypsin, cathepsin G, PP elastase and HL elastase have been measured and are published (Teshima, Griffin, and Powers, J. Biol. Chem. 257, pp 5085–5091 (1982)). The published Ki values are dissociation constants of the enzyme inhibitor complex. Significant inhibition of the enzyme will occur if the inhibitor concentration is chosen to be approximately equal to Ki. Essentially complete inhibition of the enzyme will occur if the concentration of the inhibitor is chosen to be 10 fold or more times Ki. Thus the specifity or generality of the inhibition reaction can be controlled first, by choosing the appropriate inhibitor structure and second, by choice of the inhibitor concentration utilized.

The specificity of the inhibitor can be altered by changing the nature of the R-X-Y group. The structures with the longer acyl groups such as heptafluorobutan-oyl are best at inhibiting chymotrypsin. Almost all are equally effective at inhibiting HL elastase. Only the fluoroacyl derivatives inhibit cathepsin G well and only the acyl or fluoroacyl derivatives and not the derivative where R=t-butyloxycarbonyl inhibit PP elastase well. Thus changing the size, shape and nature of the acyl group can lead either to a very specific inhibitor or to a very general inhibitor. Again the specificity or generality of the inhibition can be controlled by the concentration utilized relative to the Ki value for the specific enzyme whose inhibition is desired.

It has been found that certain heterocyclic compounds will inhibit serine proteases such as elastase, cathepsin G and chymotrypsin by reversibly blocking the enzyme. The heterocyclic compounds of this invention are 2-substituted 4H-3,1-benzoxazin-4-ones and 2-substituted 4-quinazolinones. These compounds have been widely prepared for other purposes (cf. Errende, Oien, and Yarian, J. Org. Chem., 42, pp 12–18 (1977); Patel and Patel, J. Indian Chem. Soc., 42, pp 531–535 (1965)). One derivative, 2-bromomethyl 4H-3,1-benzoxazin-4-one inactivates bovine chymotrypsin by irreversibly alkylating methionine-192 of the enzyme (cf. Alazard, Bechet, Dupaix, and Yon, Biochim., Biophys. Acta, 309, pp 379–390 (1973)). However this inhibitor is not useful either in vivo or in vitro for the uses cited in this application. Since it is an alkylating agent, it could not be used in vivo due to its potential carcinogenicity. In vitro, it could not be used in the presence of any peptides, proteins, or other molecules containing nucleophilic groups since alkylation of the nucleophilic groups would alter the activity, properties, and function of the peptide, protein or other molecule. Therefore, a need exists for a less reactive type of heterocyclic serine protease inhibitor. The novel reversible heterocyclic serine protease inhibitors of this invention have the following structural formula:

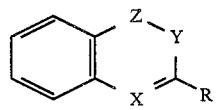

wherein
Z is selected from the group consisting of CO, SO, $SO_2$, CCl, and CF,
Y is selected from the group consisting of O, S, and NH,
X is selected from the group consisting of N and CH, and R is selected from teh group consisting of $C_{1-6}$ alkyl (such as methyl, ethyl, and propyl), $C_{1-4}$ alkyl containing a phenyl (such as benzyl), and $C_{1-6}$ floralkyl (such as trifluoromethyl, pentafluoroethyl, and heptafluoropropyl).

The Z group must be electrophilic since it interacts with the active site serine OH group of the serine protease. The R group must be unchanged and hydrophobic. One or more of the carbons in the R group could be replaced by O, S, NH and other such atomic groups as long as the R group maintains its hydrophobic character.

The following novel compounds are representative of this invention:
2-trifluoromethyl-4H-3,1-benzoxazine-4-one,
2-pentafluoroethyl-4H-3,1-benzoxazine-4-one,
2-heptafluropropyl-4H-3,1-benzoxazine-4-one,
2-methyl-4H-3,1-benzoaxazine-4-one,
2-propyl-4H-3,1-benzoaxazine-4-one,
2-benzyl-4H-3,1-benzoaxazine-4-one,
2-heptafluoropropyl-4-quinazolinone,
2-propyl-4-quinazolinone,
2-benzyl-4-quinazolinone,
2-($C_6H_5CCl_2$)-4-chloroquinazoline, and
2-propyl-4-chloroquinazoline.

Inhibition constants (Ki) for the inhibition of PP elastase, HL elastase, chymotrypsin and cathepsin G have been measured and are published (cf. Teshima, Griffin and Powers, J. Biol. Chem. 257, pp 5085–5091(1982)). The applicant was director of the research coauthored by others. It has already been described above how to use the Ki values to choose an inhibitor with specificity toward a certain enzyme or which is a general inhibitor.

To use the above identified inhibitors in vitro, they are dissolved in an organic solvent such as dimethylsulfoxide or ethanol and are added to an aqueous solution containing the protease which is to be inhibited such that the final concentration of organic solvent is 25% or less. The inhibitors may also be added as solids or in suspension.

It is well known in the literature that in vitro activity of elastase inhibitors correlates with in vivo activity in animal models of emphysema. Thus the novel inhibitors described here should be useful for the treatment of emphysema. Elastase inhibitors have been used orally, by injection or by instillation in the lungs in animal studies (cf. Powers, Am. Rev. Respir. Dis., 127, s54–s58 (1983) and references cited therein). The inhibitors described above can be used by any of these routes.

Several other diseases also involve tissue destruction by proteases such as elastase-like and chymotrypsin-like enzymes (cf. Powers, Ad. in Chem., 198, 347–367 (1982)). These include pancreatitis, inflammation, and adult respiratory syndrome. Although correlations between in vitro activity of elastase and chymotrypsin inhibitors and in vivo activity in animal models have not yet be made for these diseases, it is likely that such correlations will be made shortly. And the novel inhibitors can then be used in any cases where such correlations are made.

The following example is given to illustrate the invention and is not intended to limit it in any manner.

EXAMPLE 1

Preparation of N-Heptafluorobutanyolanthranilic Acid Thiobenzyl Ester

Anthranilic acid thiobenzyl ester hydrochloride (200 mg) was acylated with heptafluoro butyric anhydride (322 mg). The product was purified by silica gel column chromatography using chloroform as a solvent to give 256 mg of material with mp 50–51 deg centigrade.

Anal. Calcd. for $C_{18}H_{12}NO_2F_7S$: C, 49.21; H, 2.75;, N, 3.19. Found: C, 49.20; H, 2.79; N, 3.16.

Other illustrative examples are incorporated by reference herein in the Teshima, Griffin and Powers publication, cited above.

What is claimed is:

1. A compound of the formula:

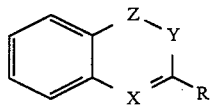

wherein
Z is CO,
Y is O,
X is N, and
R is selected from the group consisting of $C_{2-6}$ fluoralkyl, $C_{1-6}$ fluorinated alkoxy, and $C_{1-4}$ halogenated alkyl with an attached phenyl.

2. A process for the inhibition of elastase, chymotrypsin and serine proteases which cleave peptide bonds in peptides and protein between two specific amino acids —AA1—AA2— where AA1 is Ala, Asn, Cys, Gln, Gly, His, Ile, Leu, Met, Phe, Ser, Thr, Trp, Tyr, or Val and AA2 is Ala, Arg, Asn, Asp, Cys, Glu, Gln, Gly, His, Ile, Leu, Lys, Met, Phe, Pro, Ser, Thr, Tyr, or Val, comprising the step of adding to a medium containing the protease an effective amount of an inhibitor having the following structure:

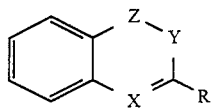

wherein:
Z is CO,
Y is O,
X is N, and
R is selected from the group consisting of $C_{1-6}$ alkyl, $C_{1-4}$ alkyl containing a phenyl, and $C_{1-6}$ fluoroalkyl.

3. A method for treating emphysema in mammalian species, comprising the step of administering to said mammalian species a therapeutically effective amount of a compound having the following structure:

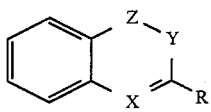

wherein
Z is CO,
Y is O,
X is N, and
R is selected from the group consisting of $C_{1-6}$ alkyl, $C_{1-4}$ alkyl containing a phenyl, and $C_{1-6}$ fluoroalkyl.

* * * * *